(12) United States Patent
May et al.

(10) Patent No.: US 7,998,750 B2
(45) Date of Patent: Aug. 16, 2011

(54) MASS SPECTROMETRY PRECURSOR ION SELECTION

(75) Inventors: Michael May, Cheshire (GB); Jingwen Yao, Cambridgeshire (GB)

(73) Assignee: Shimadzu Research Laboratory (Europe) Limited, Lancashire (GB)

( * ) Notice: Subject to any disclaimer, the term of this patent is extended or adjusted under 35 U.S.C. 154(b) by 274 days.

(21) Appl. No.: 11/884,676

(22) PCT Filed: Feb. 17, 2006

(86) PCT No.: PCT/GB2006/000560
§ 371 (c)(1),
(2), (4) Date: Aug. 20, 2007

(87) PCT Pub. No.: WO2006/087565
PCT Pub. Date: Aug. 24, 2006

(65) Prior Publication Data
US 2008/0315081 A1    Dec. 25, 2008

(30) Foreign Application Priority Data
Feb. 18, 2005  (GB) .................................. 0503411.1

(51) Int. Cl.
*G01N 24/00*    (2006.01)

(52) U.S. Cl. ............ 436/173; 436/86; 702/19; 250/281; 250/282

(58) Field of Classification Search ........................ None
See application file for complete search history.

(56) References Cited

FOREIGN PATENT DOCUMENTS
WO    03102572    12/2003

OTHER PUBLICATIONS

Anderson et al.: "A new Algorithm for the evaluation of shotgun peptide sequencing in proteomics: Support vector machine classification of peptide MS/MS spectra and SEQUEST scores.", Journal of Proteome Research, vol. 2, No. 2, 2003, pp. 137-146.
Papayannopoulos I A: "The Interpretation of Collision-Induced Dissocation Tandem Mass Spectra of Peptides", Mass Spectrometry Reviews, John Wiley and Sons, New York, NY, US, vol. 14, 1995, pp. 49-73.
Jensen O N et al.: "Automation of matrix-assisted laser desorption/ionization mass spectrometry using fuzzy logic feedback control." Analytical Chemistry. May 1, 1997, vol. 69, No. 9, pp. 1706-1714.

*Primary Examiner* — Yelena G Gakh
*Assistant Examiner* — Robert Xu
(74) *Attorney, Agent, or Firm* — Jacobson Holman PLLC

(57) ABSTRACT

The present invention is concerned with methods for the selection of precursor ions of a sample polypeptide for fragmentation in mass spectrometry, together with methods for determining at least one putative amino acid sequence for a sample polypeptide, apparatus and computer programs for same.

6 Claims, 6 Drawing Sheets

GAP

INTENSITY

MASS SPECTROMETRY PRECURSOR ION SELECTION

This is a national stage of PCT/GB06/000560 filed Feb. 17, 2006 and published in English.

The present invention is concerned with methods for the selection of precursor ions of a sample polypeptide for fragmentation in mass spectrometry, together with methods for determining at least one putative amino acid sequence for a sample polypeptide, apparatus and computer programs for same.

Mass spectrometry is an increasingly important tool for identifying protein samples. It is currently well known in the art to use mass spectrometry to confirm the identity of a sample protein/polypeptide (the two terms are interchangeable herein unless stated otherwise). Protein mass fingerprinting programs such as MASCOT (based on the MOWSE algorithm) use mass spectrometry data generated from the enzymatic digestion (using e.g. Trypsin) of a protein to attempt to identify it from primary sequence databases (Matrix Science Ltd, GB; Perkins et al., Electrophoresis. 1999 December; 20(18):3551-67; PMID: 10612281). Approaches to identifying proteins from mass spectrometry data include the use of peptide molecular weights (in the form of mass to charge ratios) from the digestion of a protein by an enzyme. Other approaches use tandem mass spectrometry data from one or more peptides (also known as MS/MS and $MS^2$), an ion species of interest being selected and fragmented to give hierarchical product ion spectra. Still others combine mass data with amino acid sequence data. Fuzzy logic systems have been used to control laser fluence in MALDI mass spectrometry systems—Jensen ON et al. (Anal Chem. 1997 May 1; 69(9):1706-14; PMID: 9145026).

WO 03/102572 provides a method for determining at least one de novo putative (i.e. candidate) amino acid sequence for a sample polypeptide. The invention disclosed therein is particularly useful when using $MS^n$ mass spectrum data where n>=2. Herein, it is referred to as the "Sequencer".

However, the generation of higher level $MS^n$ mass spectral data requires the selection of ion peaks (i.e. m/z peaks) to act as precursor ions for further fragmentation, and this presently requires expert input in order that the optimal selection is made. Thus, in order to obtain the best possible results from WO 03/102572 (and other mass spectral techniques) it is necessary for the selection of m/z peaks (i.e. precursor ions) for fragmentation to be made by an expert.

When seeking to determine a putative amino acid sequence for a sample polypeptide, particular situations can arise in which it is necessary to perform a further fragmentation on at least one m/z peak of a mass spectrum. For example, when using a MALDI-QIT spectrometer, the limit of the ion trap in the instrument causes the ions having a mass of one-third or less of the mass of the precursor to be undetectable. Similarly, it is also typically not possible to observe fragment ions in the lower-third mass range. In order to derive further mass spectrum data relating to the undetectable regions, m/z peaks from the mass spectrum must be selected to act as precursor ions for further fragmentation to provide information. This process can theoretically go further to obtain tandem spectra of a parent peptide, $MS^n$.

Current methods of precursor ion selection are mainly dependent on the intensity of m/z peaks. The strongest peak in a spectrum may be selected as a precursor ion for the next spectrum (i.e. for further fragmentation). As mentioned above, this selection is usually carried out by way of a visual inspection of a mass spectrum by an expert. This is obviously an expensive approach, and is also dependent upon the availability of an appropriate expert. Further, such a method does not guarantee that a correct m/z peak will be selected.

In particular, it is desirable to ensure that inappropriate m/z peaks are not selected to be used as precursor ions for further fragmentation. For example, it can be desirable to ensure that e.g. chemical noise peaks, or internal ions are not used as precursor ions.

Mass spectrum techniques provide the opportunity for high speed, high-throughput de novo sequencing of polypeptides, and the need and desire is for this to be an automated technique, requiring as little human intervention as possible. In particular, there is a need to dispose with the requirement for an expert, in order that a mass spectrum device can simply be provided with a sample polypeptide for analysis and that it can then determine an amino acid sequence for the sample polypeptide by de novo sequencing or database searching methods, the amino acid sequence being for as large a part of the sample polypeptide amino acid sequence as possible and having a high probability of being correct.

The present invention seeks to overcome the prior art disadvantages and address the above issues. In particular, the present invention may be used with WO 03/102572, as well as with other methods and techniques which determine at least one putative (i.e. candidate) amino acid sequence from a mass spectrum, and where at least one m/z peak needs to be selected for use as a precursor ion for further fragmentation.

According to the present invention there is provided a method for selecting a precursor ion of a soft ionisation mass spectrum of a partially degraded sample polypeptide for fragmentation, said soft ionisation mass spectrum comprising a set of m/z peaks of ion species obtained from said partially degraded sample polypeptide, said method comprising the steps of:

(i) determining at least two candidate m/z peak sets from said soft ionisation mass spectrum of said partially degraded sample polypeptide, each m/z peak in each candidate m/z peak set differing from its at least one neighbour by the mass of an amino acid, and determining a putative amino acid sequence from each candidate m/z peak set, each amino acid sequence being that of the amino acids which correspond to the mass differences between each m/z peak and its at least one neighbour; and (ii) analysing using an artificial intelligence technique said m/z peaks of said at least two candidate m/z peak sets, to select at least one m/z peak for fragmentation.

In particular, fuzzy logic techniques can be used as the artificial intelligence techniques, as detailed below. However, other artificial intelligence techniques can be used as an alternative or in addition to fuzzy logic techniques, and these include but are not limited to: data mining techniques, artificial neural networks, decision trees, genetic algorithms, and rule induction systems such as C4.5 and machine learning techniques.

As detailed below, the rules used in the fuzzy logic technique are based on the knowledge and expertise in those selected variables corresponding to the mass spectra. From these rules, a determination of the suitability of a candidate m/z peak as a precursor ion is made. As an alternative to or in addition to fuzzy logic, data mining methods, e.g. neural network, decision tree and genetic algorithms may be used to find these rules for a specific instrumental data set. These methods usually derive the conclusion from a set of experimental data through training. The training data set could be all the mass peaks taken from the specific spectra with relative intensity values.

Once a model has been created by the applications of these methods, the model can be used to predicate new data. It can be independently applied to a new data set to select a precursor ion from the model. If it is combined with the fuzzy logic system to have an on-line control system (for example to control a selection of a possible precursor ion), the model derived from these methods could be formed in the rulebase to help the artificial intelligent decision making by the fuzzy logic technique. It is possible to use different numbers of variables to define the model from different methods.

Typically, three kinds of data mining techniques are used in the creation of prediction model-neural networks, decision tree and rule induction systems. Neural networks provide an answer in a numerical format if the predicate rules can be found (e.g. which peak is selected as precursor ion/which one is not). Rule induction systems, when used for prediction, may give more explanation of a decision, with comparison of different derived rules, and an indication of which one should be better than another one. Neural networks may be a more suitable data mining algorithm to implement into this system.

The accuracy and coverage for the rules or predictive models derived from these methods are important to determine a practical use in this system. Recognition and making explicit of the uncertainty in the rule will directly affect selection results by fuzzy logic. The coverage represents the amount of data involved in these rules or applied to the rules. High coverage may give a more reliable result.

In particular, the process of selecting an m/z peak to act as a precursor ion for further fragmentation in mass spectrometry can be used in the techniques of WO 03/102572, although of course it is not limited to use with such techniques. Other techniques may be used to generate putative amino acid sequences for a sample polypeptide, and the method of the present invention may be equally applied to them where it is necessary to decide upon an m/z peak for further degradation.

When certain amino acids are detected in the derived series of putative amino acid sequence, e.g. aspartic acid with C-terminated arginine tryptic peptide, etc. it may give guidance to predict possible peaks with high intensity in the further fragment spectrum since these amino acids will provide favoured cleavage sites according to their specific chemical structure or properties.

By the "at least one neighbour" of an m/z peak is meant the closest m/z value above and/or below the m/z peak value. So, for example, in a nominal set of m/z peaks having values 375, 300, 347, 372 and 331, the peak value 331 has two neighbours, namely 300 and 347.

The sample polypeptide mass can be at least 3000 Da, for example at least 4000, 5000, 6000, 7000, 8000, 9000, 10000 or 15000 Da. The partial degradation of the sample polypeptide can result in fragments having masses of up to e.g. 3000 or 4000 Da.

The soft ionisation mass spectrum can give at least 3 m/z peaks, for example at least 4, 5, 6, 7, 8, 9, 10, 15, 20, 25, 30, 40, 50, 75 or 100 m/z peaks.

Each candidate m/z peak set can comprise at least 3 m/z peaks, for example at least 4, 5, 6, 7, 8, 9, 10, 15, 20, 25, 30, 40 or 50 m/z peaks.

The analysis using artificial intelligence techniques, for example fuzzy logic principles, may be made using input variables representing at least 2, 3 or all 4 of:
(a) the number of amino acids corresponding to the difference between the candidate m/z peak value and the closest terminal m/z peak value of the at least one other candidate m/z peak set; (this is also referred to as GAP)
(b) the intensity of the candidate m/z peak; (this is also referred to as INTENSITY)
(c) the mass represented by the candidate m/z peak value; (this is also referred to as LOW_VALUE_CRITERION~) and
(d) the number of amino acids in the longest of any putative amino acid sequence corresponding to any candidate m/z peak set containing the candidate m/z peak (this is also referred to as MASS_SERIES).

A further explanation for the MASS_SERIES variable of (d) is that when any candidate m/z peak is involved in a P-series (i.e. a candidate m/z peak set), the number of amino acids in the series is defined as the variable. If the candidate m/z peak is involved in several P-series, the number of amino acids in the longest of these series is taken.

| e.g. | $[\ldots m_a, \ldots m_i, \ldots]$ | (1) | 5 amino acids |
|---|---|---|---|
| | $[\ldots m_a, m_i, \ldots]$ | (2) | 4 amino acids |
| | $[\ldots m_a, \ldots m_i, \ldots, m_j, \ldots]$ | (3) | 9 amino acids |

$m_a$ is the candidate mass peak, which is involved in three different series (1), (2) and (3). 9 is taken as the length for this candidate (since it is the greatest length) and is then converted to a percentage value to the predicated correct amino acid sequence length for the sample polypeptide. If the predicated length for the sample is 14 amino acids, the variable for this candidate is 9/14=0.64. The predicated length can be calculated on the precursor ion mass using the average value of all standard amino acid masses. A tolerance value (e.g. 2-4) can also be applied for determining the length.

As can be done with the determination of candidate m/z peak sets, the set of amino acid masses used to estimate the length of the sample polypeptide may simply consist of the masses of standard amino acids. Alternately, if it is known that a sample polypeptide does not comprise a certain amino acid then the mass of that certain amino acid can be excluded. Similarly, amino acid masses of e.g. chemically and/or post-translationally modified amino acids can also be used. The masses of other amino acids, both naturally occurring and synthetic, can also be used, and can include modified and unusual amino acids such as 2-aminoadipic acid, 2-aminobutyric acid, isodesmosine, 6-n-methyllysine, and norvaline. Others are listed in for example Table 4 of WIPO Standard St.23. Similarly, allowance can be made for isotopically labelled amino acids. Thus this can be used to form the predicate for determining an estimated (i.e. predicated) length for the sample polypeptide.

The present invention can make use of a fuzzy expert system whose general inference process comprises four steps: Fuzzification, Inference, Composition and Defuzzification. Thus the analysis using fuzzy logic principles may comprising the steps of:
(i) fuzzification of said input variables on at least one membership function;
(ii) inference of a plurality of rules of a rulebase, each rule having at least one output variable, to define a fuzzy subset for each output variable for each rule;
(iii) composition of said fuzzy subsets of said inference step (ii) to define a fuzzy output set comprising a single output subset for each of said at least one output variable; and
(iv) defuzzification of said fuzzy output set to a crisp number.

Fuzzification

The input variable of step (a) can be used in a fuzzification step in which membership functions defined on the input variable are applied to the actual value, and the degree of truth for each rule premise (e.g. GAP is SMALL, GAP is MEDIUM, and GAP is LARGE) determined.

Of course, alternative membership functions may be defined on the GAP input variable, e.g. GAP is SMALL, GAP is SMALL TO MEDIUM, GAP is MEDIUM, GAP is MEDIUM TO LARGE, GAP is LARGE, and GAP is VERY LARGE. Thus the degree of membership of the GAP input variable (i.e. a member of the GAP set) in each of the fuzzy subsets (SMALL, MEDIUM, LARGE etc.) can be determined.

GAP is defined in terms of the number of amino acids equivalent to the difference between the candidate m/z peak value and the closest terminal m/z peak value of the at least one other candidate m/z peak set.

Thus, if the candidate peak is greater than the m/z peak at the high end of the at least one other candidate m/z peak set, the difference is between the candidate peak and the peak at the high end. If the candidate peak is less than the peak at the low end of the at least one other candidate m/z peak set, the difference is between the candidate peak and the peak at the low end of the series.

| e.g. | $[m_1, m_2, \ldots m_n]$ | series 1; |
| --- | --- | --- |
| | $[M_1, M_2, \ldots M_n]$ | series 2; | the GAP could be taken as GAP = $M_1$ [ ] $m_n$;

Since amino acids vary in mass with the lightest standard amino acid, Glycine, having a mass of 57.02 Da and the heaviest standard amino acid, Tryptophan, having a mass of 186.08 Da, if a SMALL GAP is considered to be less than one amino acid then the membership function for GAP is SMALL gives a value ranging from 1 for a difference <=57.02 Da to a value of 0 for differences >186.08 Da. Similarly, if a MEDIUM GAP is considered to be two amino acids then the membership function for GAP is MEDIUM gives values of 0 for a difference of <114.04 Da or >372.16 Da and a value greater than 0 in between. Similarly, if a LARGE GAP is considered to be >=4 amino acids then the membership function for GAP is LARGE gives a value ranging from 0 for a difference of <228.08 Da to a value of 1 for a difference >558.24 Da.

In particular, the analysis using fuzzy logic principles may require that a GAP is large, where LARGE is considered to be >=3 amino acids. When MALDI-QIT data is used, GAP may be defined in terms of the number of amino acids equivalent to the difference between the candidate m/z peak value and the low end terminal peak value of the at least one other candidate m/z peak set. Alternative fuzzification steps and rulebases which favour low mass candidate m/z peaks are described in the specific embodiment below, and apply equally to other embodiments of the invention.

The generating of sets of candidate m/z peaks and the membership functions can be affected by the amino acid masses with which the mass differences are compared. For example, the set of amino acid masses may simply consist the masses of standard amino acids. Alternately, if it is known that a sample polypeptide does not comprise a certain amino acid then the mass of that certain amino acid can be excluded. Similarly, amino acid masses of e.g. chemically and/or post-translationally modified amino acids can also be used. The masses of other amino acids, both naturally occurring and synthetic, can also be used, and can include modified and unusual amino acids such as 2-aminoadipic acid, 2-aminobutyric acid, isodesmosine, 6-n-methyllysine, and norvaline. Others are listed in for example Table 4 of WIPO Standard St.23. Similarly, allowance can be made for isotopically labelled amino acids.

Thus, for example the GAP membership function can be modified in light of the knowledge that a given amino acid in a sample polypeptide is isotopically labelled, and this can help ensure the accuracy of the fuzzification of the GAP values.

The membership functions used may be any appropriate membership function, for example a Z-type, π-type or S-type. Examples of standard membership functions are described further in e.g. Constantin von ("Fuzzy Logic and NeuroFuzzy Application in Business and Finance"; pp 327-328; Prentice Hall PTR, New Jersey, 1997).

The input variable of step (b) can be used in a fuzzification step in which membership functions defined on the input variable are applied to the actual value, and the degree of truth for each rule premise (e.g. INTENSITY is LOW, INTENSITY is MEDIUM, and INTENSITY is HIGH) determined.

The most abundant m/z peak (i.e. the one with the greatest intensity on the mass spectrum) is de facto considered to be in the HIGH INTENSITY fuzzy subset of the INTENSITY set and can be given a value of 100.0. The value attributed to the less abundant m/z peaks can then be calculated relative to the most abundant m/z peak to give an input variable. The membership functions defined on the input variable (e.g. INTENSITY is LOW, INTENSITY is MEDIUM, and INTENSITY is HIGH) can then be applied to the actual value, and the degree of truth for each rule premise determined.

For example, when the intensity is <=10, the membership function for INTENSITY is LOW can give a value of 1. When the intensity is >20, the membership function for INTENSITY is LOW can give a value of 0. The membership function for INTENSITY is MEDIUM can give a value of 0 when the intensity is <=18 or >55, and a value of greater than 0 in between. In the intensity range of >18 to <=32, the value increases linearly, MEDIUM keeps a value of 1 when the intensity is between >32 and <=55. The membership function for INTENSITY is HIGH can give a value of 0 when the intensity is <=50 and increases linearly with increasing intensity, giving a value of 1 when the intensity is >=56.

In particular, a high intensity peak can be of particular interest and a strong candidate for further fragmentation even if it is located at the interior of a candidate m/z peak set rather than at a terminus—this is because high intensity peaks can give high quality fragmentation, allowing e.g. the determination of additional lower end ions, especially in ion trap spectra. Combining the series of such further fragmentation with the parent/previous ion series can help derivation of a complete sequence for a sample polypeptide. Hence this INTENSITY value can be weighted appropriately.

The input variable of step (c) can be used in a fuzzification step in which membership functions defined on the input variable are applied to the actual value, and the degree of truth for each rule premise (e.g. LOW_VALUE_CRITERION is LOW, and LOW_VALUE_CRITERION is HIGH) determined. The input variable is the candidate m/z peak value. For example, the membership function for LOW_VALUE_CRITERION is LOW can give a value of 1 for an m/z value of <=450 and a value of 0 for an m/z value of >525. The membership function for LOW_VALUE_CRITERION is HIGH can give a value of 0 for an m/z value of <475 and a value of 1 for an m/z value >=550.

In particular, for a low mass value at the end of or in a candidate m/z peak set, there is little sense in performing further fragmentation. However, care needs to be taken to ensure that peaks which may be worth using as precursor ions are not excluded by inferences drawn on the LOW_VALUE_CRITERION variable.

The input variable of step (d) can be used in a fuzzification step in which membership functions defined on the input variable are applied to the actual value, and the degree of truth for each rule premise (e.g. MASS_SERIES is LOW, MASS_SERIES is MEDIUM, and MASS_SERIES is HIGH) determined. The input value is the ratio of the number of amino acids in the longest of any putative amino acid sequence corresponding to any candidate m/z peak set containing the candidate m/z peak to the predicted length of the given peptide sample. For example, the membership function for MASS_SERIES is LOW can give a value of 1 for <=0.2 and a value of 0 for >0.35. The membership function for MASS_SERIES is MEDIUM can give a value of 0 for <=0.30 and >0.75, and a value >0 in between, with a value of 1 for a ratio value at 0.5 and before this point, the value increases linearly from 0 and decreases from this point. The membership function for MASS_SERIES is HIGH can give a value of 0 for <=0.60, and a value of 1 for >0.8, and a value of >0 in between.

The above membership functions for the GAP, INTENSITY, LOW_VALUE_CRITERION and MASS_SERIES sets are given as examples only—alternative or additional fuzzy subsets may be defined within the sets, and the membership functions may be altered.

With the degree of truth for each premise (e.g. INTENSITY is HIGH) having been calculated, this can then be used in the rulebase (also referred to as a "knowledge base") of a fuzzy expert system.

Inference

Once the fuzzification steps have been completed, an inference step is then applied to calculate a truth value for the premise of each rule, and applied to the conclusion part of each rule, giving a degree of validity for the rule (and giving a linguistic output). The output (the degree of validity for the rule) can be a variable POSSIBLE_SELECTION representing the rating of the m/z peak by the rule for further selection as a precursor ion. The linguistic output of the variable POSSIBLE_SELECTION can be determined via a further set of membership functions for e.g. POSSIBLE_SELECTION is LOW, POSSIBLE_SELECTION is MEDIUM, and POSSIBLE_SELECTION is HIGH.

In one example, the GAP input variable has the fuzzy subsets of SMALL, MEDIUM and LARGE; the INTENSITY input variable has the fuzzy subsets of SMALL, MEDIUM and LARGE; the LOW_VALUE_CRITERION input variable has the fuzzy subsets of LOW and HIGH; and the MASS_SERIES input variable has the fuzzy subsets of LOW, MEDIUM and HIGH. This gives a total of 54 different possible combinations of the fuzzy subsets of the input variables, and each one resolves to a fuzzy subset of the POSSIBLE_SELECTION variable having a value of LOW, MEDIUM or HIGH.

Examples of three of these combinations are given in Table 1 (below). For example, Rule 1 represents the following evaluation: IF GAP is SMALL and INTENSITY is LOW and LOW_VALUE_CRITERION is LOW and MASS_SERIES is LOW THEN POSSIBLE_SELECTION is LOW.

TABLE 1

| Condition | | | | | THEN |
|---|---|---|---|---|---|
| Gap | Intensity | Low_Value_Crit | Mass_Series | DoS | PossibleSel |
| small | low | low | Low | 1.00 | Low |
| small | low | low | Medium | 1.00 | Low |
| small | low | low | High | 1.00 | Low |

Note:
DoS = Degree of Support

In the processing of the above rulebase, the MAX-MIN method is typically used. The minimum operator is a generalization of the boolean 'AND'; the maximum operator is a generalization of the boolean 'OR'. Using standard MAX-MIN/MAX-PROD methods for input variables, the individual importance of a rule can be expressed only as a 0 or 1, and this can result in a wrong selection being made by a system when a value exists with more uncertainty related to each variable term. An alternative way to solve the problem is that each rule is assigned a degree of support (DoS) representing the individual importance of the rule. Rules themselves can be "fuzzy", with validity between 0 and 1. All 54 fuzzy rules can be examined and tested using test data and the DoS values assigned to each rule and output terms (POSSIBLE_SELECTION is LOW, MEDIUM, and HIGH) can be modified accordingly. For instance, Rules 24 and 25 (below) infer to medium as the output variable. From one high positive relative variable, "Intensity", which has the most important influence in the selection, Rule 24 defines as low, while Rule 25 as medium. The DoS value is assigned as 0.3 for Rule 24, while the other high positive variable, "Low_Value_Crit", in Rule 25 is defined as low, and a DoS value of 0.9 is given. If, for example, the degree of validity of the conditions are all 0.6 matching these two rules, using the product operator for composition, Rule 24:
  IF "Gap"=medium AND "Intensity"=low AND "Low_Value_Crit"=high AND "Mass_Series"=high THEN "PossibleSel"=medium;

Rule 25:
  IF "Gap"=medium AND "Intensity"=medium AND "Low_Value_Crit"=low AND "Mass_Series"=low THEN "PossibleSel"=medium;

the result of the rules would be:
Θ {Degree of Validity in the IF Part, Degree of Support}
:=Result of the Rule (Validity in the THEN part)
that is,
  for Rule 24: Θ {0.6,0.3}=0.18.
  for Rule 25: Θ {0.6,0.9}=0.54.

This means that the result for "PossibleSel" medium is a degree of validity of 0.18 for Rule 24, and 0.54 for Rule 25. Thus the importance of Rule 24 is reduced.

As above, each combination in Table 1 results in one of three possibilities in the output variable. All four input variables have a positive relationship with the output variable. The input variables LOW_VALUE_CRITERION and INTENSITY are given more weight than other input variables. Fuzzy MAX-MIN logic can be used to aggregate the results from more than one fuzzy rule invoked on the same term. As is expected from the definition of the input variables, the GAP value for a candidate m/z peak should not be small if it is to be considered for use as a precursor ion. However, even if GAP is small then in combination with other values (INTENSITY, LOW_VALUE_CRITERION and MASS_SERIES), it may result in POSSIBLE_SELECTION is MEDIUM. The DoS values can be modified in order to weight the overall importance of the various rules and combinations of terms.

Additional rules can be included at the inference stage, particularly with a candidate m/z peak set which contains numerous candidate m/z peaks to be considered as candidates for further fragmentation. For example, rules based upon the INTENSITY variable can strongly favour the POSSIBLE_SELECTION value allocated to a candidate m/z peak if its INTENSITY is HIGH. However, the position of the candidate m/z peak in a candidate m/z peak set containing it (for example the longest candidate m/z peak set or the one with the lowest terminal value) can be important, and can be taken into consideration by the rulebase. Thus, for example, the following additional rule can be introduced:

IF $(P_m-P_n)$ is an amino acid mass AND intensity of $P_m > I_i$ THEN high possibility wherein:

$I_i$ is defined as a high intensity value $P_m$ is defined as the mass of the possible selected ion with the strong intensity $P_n$ is defined as an adjacent mass value in the given series The output from the rulebase need not be a linguistic one, and instead can be returned as a numerical one which can more accurately represent the degree of validity of the rule. The output value for each rule can be calculated using e.g. fuzzy MAX-MIN or MAX-PRODUCT logic, giving a numerical value calculated as a function of the truth values of the premises of each rule.

For example, with a defined input part (IF) having three variables (V1, V2 and V3), each of V1, V2 and V3 having three terms (high(h), medium(m) and low(l)), the output variable contains four terms (low, medium-low, medium-high and high). The fuzzy rules give that when the three variables have the same linguistic terms, e.g. V1=medium, V2=low, and V3=low, they may derive to different terms in the output part (THEN) by virtue of different DoS values. The details are given in Table 1A (below). For the four variables that have the same terms in the input part, they give output as very-low(v-l), low(l), high(h) and very-high(v-h) and are accompanied with a value of degree of validity.

If the MIN operator is used for this set of rules:

MIN {Degree of Validity (V1=med.), Degree of Validity (V2=low), Degree of Validity (V3=low)}:=Validity of the condition, i.e. MIN {0.33,1.00,0.67}=0.33.

TABLE 1A

| V1 | V2 | V3 | Degree of Validity for V1, V2 and V3 | | | DoS | Output |
|---|---|---|---|---|---|---|---|
| m | l | l | 0.33 | 1.00 | 0.67 | 0.00 | v-l |
| m | l | l | 0.33 | 1.00 | 0.67 | 0.04 | l |
| m | l | l | 0.33 | 1.00 | 0.67 | 0.16 | h |
| m | l | l | 0.33 | 1.00 | 0.67 | 0.06 | v-h |

This means that aggregation of the degree of validity of this precondition is given as 0.33.

If desired, the output value can also be weighted, e.g. a Degree of Support (DoS) can be allocated to each rule, and each rule thereby weighted according to its importance.

The Degree of Support provides an opportunity for the method of the present invention to be optimised without altering the rulebase. Thus, for example, a machine learning system such as an artificial neural network system can be taught to optimise its selection of m/z peaks for further degradation. For example, an expert human operator can be provided with a mass spectrum from which a selection of at least one m/z peak for further degradation can be made. The machine learning system can be provided with the same input data from which is derived an output as a selection of at least one m/z peak for further degradation, and this output can be compared to that provided by the human expert (the desired result) and the desired result used to effect learning by the machine learning system. Multiple rounds of learning can be used to effect an optimisation of the system, and the learning can be effected by a manipulation of the Degree of Support values for the rules.

This use of hypothetical and testing data can be used to optimise the system by way of modifying Degrees of Support, as detailed above. Alternatively or additionally, the membership function(s) can be modified on the basis of the hypothetical/test data. Alternatively or additionally, the rules of the rulebase can be modified on the basis of the hypothetical/test data.

Composition

With the output values from the rules of the rulebase having been calculated (and weighted as appropriate), a composition step is then used to combine together the results (i.e. the fuzzy subsets) obtained from the rulebase.

The composition is implemented by a composition operator to examine the validity of a conclusion of a rule from the rulebase. The operator is computed on this validity and degree of support, which represents a validity of the entire condition. A commonly used composition operator is a product operator, which is the product of the validities. For the previous given example, a rule from the rulebase for the IF part is:

IF V1=low AND V2=low and V3=medium. A validity of the condition has been derived as 0.33 from a MIN operator. Corresponding to the THEN part, which is medium-high, a degree of support is given as 0.16, and then composition using product operator gives the result:

$$\Theta\{0.33, 0.16\} = 0.05.$$

This gives validity of the consequence of the rule, and the result for Output medium-high is a degree of validity of 0.05.

Defuzzification

Finally, a defuzzification step is used to convert the fuzzy output set from the composition step into a crisp number, which in this case represents a rating value for the candidate m/z peak for fragmentation (i.e. for use as a precursor ion in further fragmentation). A wide range of defuzzification methods are well known in the art, and include the centroid and maximum methods.

For example, a Centre of Maximum (CoM) method can be used. Because more than one output term can be evaluated as valid, the defuzzification method must compromise between different results. The CoM computes a crisp output as a weighted mean of the term membership maxima, weighted by the inference results. The formula is Equation 1.

$$Y = \frac{\sum_{i=1}^{n} P_i \cdot Y_i}{\sum_{i=1}^{n} P_i}$$

Equation 1 where $Y_i$ is the centre of gravity of the three membership values for low, medium, high. They may be defined as e.g.: $Y_{low}=0.175, Y_{medium}=0.500, Y_{high}=0.850$ for this system. $P_i$ is the weight from the inference results. A special case in using this method is that only one output term is evaluated and similarly, a validity of the condition is also inferred from a single term. Especially when the degree of validity ($P_i$) of this term is very low (e.g. <0.28), the results may not be very appropriate to a practical case. The validity value in this case is completely ignored because it is cancelled out each other from the formula. Thus, no matter which term in the output is inferred, it always gives as the maximum value of the term. The importance of any DoS value is thus eliminated.

In order to include the influence specified in the DoS value, Equation 1 can be modified to give Equation 2:

$$Y = \frac{C \sum_{i=1}^{n} P_i^2 \cdot Y_i}{\sum_{i=1}^{n} P_i} \quad \text{Equation 2}$$

The validity value $P_i$ is considered in this case and a weight factor is added to adjust the final output value according to the value of $P_i$. Some mass values are corrected in the selection by using the modified formula. For instance, a value is inferred to the three terms as 0.0, 0.04, 0.0 in validity. For example, only the term medium may have a small weight value, 0.04. If Equation 1 is used this will result in the output value at the maximum of the medium, 0.5, which indicates that the selection has 100% possibility at the medium term. But this may correspond to a noise peak. The calculation is as follows:

$$Y = \frac{0.00 * 0.175 + 0.04 * 0.500 + 0.00 * 0.850}{0.00 + 0.04 + 0.00} = 0.5; \text{ from Equation (1)}$$

Equation 2 also relies on the value of $P_i$ and the result reduces the importance of this term. This will be finally determined by the output variable membership function. If it has a small $P_i$ value, the result will give a final output value of low.

Using the above membership functions, input values can be evaluated and an at least one rule can be applied to the membership function outputs in order to define a fuzzy expert system.

Examples of systems using linguistic rules include e.g. Virant-Klun I et al. (Comput Biomed Res. 1999 August; 32(4):305-21; PMID: 10469527) which discloses a control system based upon linguistic rules directly.

Also provided according to the present invention is a method for determining at least one putative amino acid sequence for a partially degraded sample polypeptide said method comprising the steps of:
(i) obtaining a soft ionisation mass spectrum of said partially degraded sample polypeptide giving a set of m/z peaks of ion species obtained from said partially degraded sample polypeptide;
(ii) determining at least two candidate m/z peak sets from said soft ionisation mass spectrum, said soft ionisation mass spectrum comprising a set of m/z peaks of ion species obtained from said partially degraded sample polypeptide, each m/z peak in each candidate m/z peak set differing from its at least one neighbour by the mass of an amino acid, and determining a putative amino acid sequence from each candidate m/z peak set, each amino acid sequence being that of the amino acids which correspond to the mass differences between each m/z peak and its at least one neighbour;
(iii) analysing using artificial intelligence techniques, for example fuzzy logic principles, said m/z peaks of said at least two candidate m/z peak set, to select at least one m/z peak for fragmentation;
(iv) obtaining a further soft ionisation mass spectrum of said selected at least one m/z peak, giving a set of m/z peaks of ion species;
(v) optionally repeating steps (ii)-(iv), using at least two of the previously obtained soft ionisation mass spectra as the said soft ionisation mass spectrum; and
(vi) determining an at least one candidate m/z peak set from said soft ionisation mass spectra, said soft ionisation mass spectra comprising a set of m/z peaks of ion species obtained from said partially degraded sample polypeptide, each m/z peak in each candidate m/z peak set differing from its at least one neighbour by the mass of an amino acid, and determining a putative amino acid sequence from each candidate m/z peak set, each amino acid sequence being that of the amino acids which correspond to the mass differences between each m/z peak and its at least one neighbour.

Also provided according to the present invention is apparatus for selecting a precursor ion of a soft ionisation mass spectrum of a partially degraded sample polypeptide for fragmentation, comprising:
(i) data input means;
(ii) data storage means having stored thereon a fuzzy logic rulebase;
(iii) data processing means comprising program code for carrying out a method according to the present invention; and
(iv) data output means for outputting the output of the data processing means.

The apparatus may comprise a mass spectrometer.

Also provided according to the present invention is a computer program product for selecting at least one m/z peak of a soft ionisation mass spectrum of a partially degraded sample polypeptide for fragmentation, said computer program comprising program code for analysing using an artificial intelligence technique the m/z peaks of at least two candidate m/z peak sets to select at least one m/z peak for fragmentation, said at least two candidate m/z peak sets determined from said soft ionisation mass spectrum of said partially degraded sample polypeptide, said soft ionisation mass spectrum comprising a set of m/z peaks of ion species obtained from said partially degraded sample polypeptide, each m/z peak in each candidate m/z peak set differing from its at least one neighbour by the mass of an amino acid, and a putative amino acid sequence being determined from each candidate m/z peak set, each putative amino acid sequence being that of the amino acids which correspond to the mass differences between each m/z peak and its at least one neighbour. Again, said artificial intelligence technique may comprise fuzzy logic principles.

The invention will be further apparent from the following description, with reference to the several figures of the accompanying drawings, which show, by way of example only, one form of selection of at least one m/z peak from an m/z peak set for further fragmentation. Of the figures.

Figure 1:
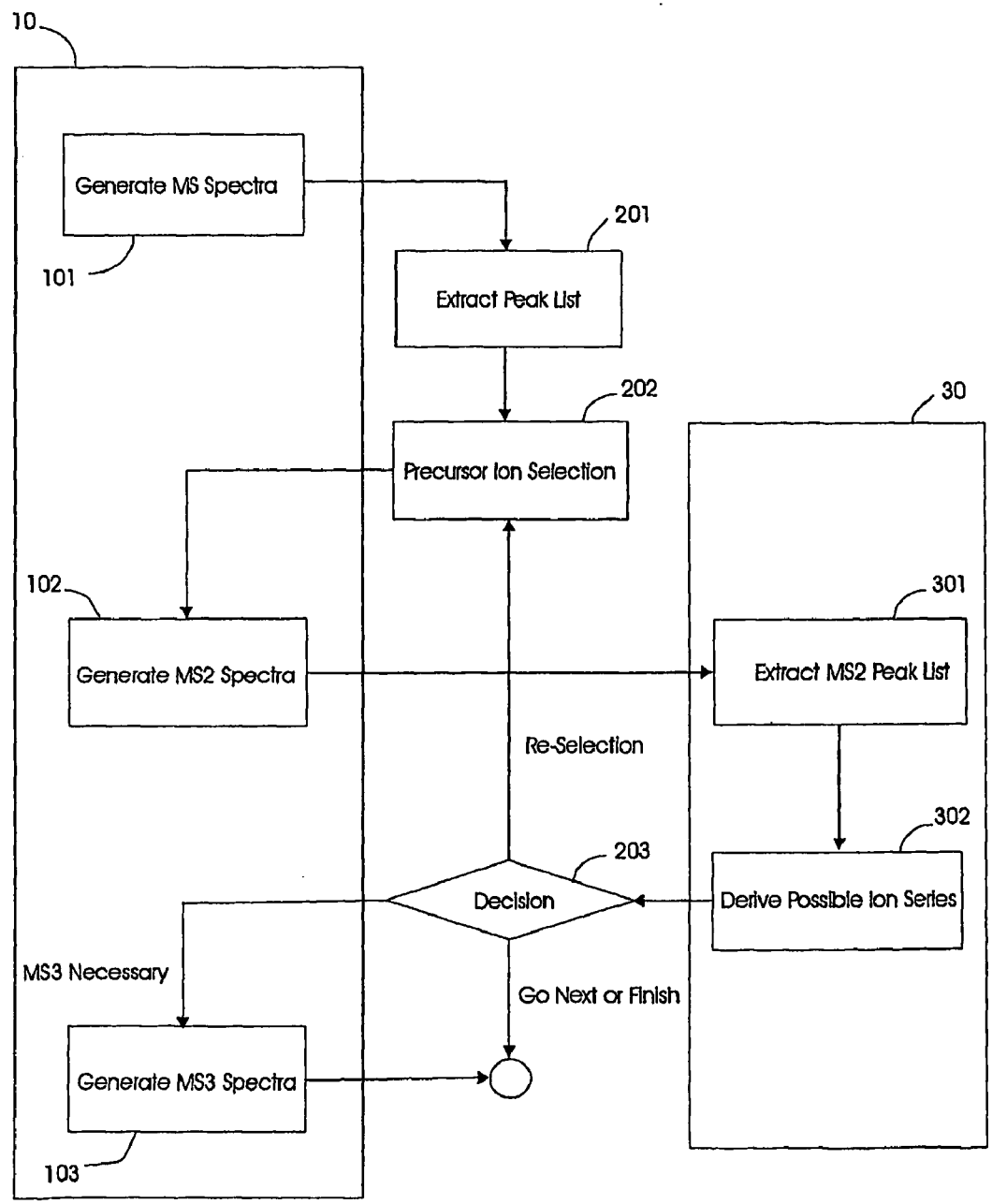
FIG. 1 is a flow chart showing the process of precursor ion selection for tandem mass spectra.

In an example system according to the present invention, a MALDI-TOF mass spectrometer (not shown) generates an MS spectrum 110 of a tryptically digested sample polypeptide. A mass list containing m/z and intensity values is extracted from the spectrum 110 at step 201 and a precursor ion peak selected from a peptide ion mass at step 202 for further ionisation to give an $MS^2$ spectrum 102. A mass list 301 containing m/z and intensity values is extracted from the $MS^2$ spectrum 102, and mass list 301 is then inputted into sequence generator 302 as described in WO 03/102572 and at least two candidate amino acid sequences for the sample polypeptide are determined.

Decision step 203 uses fuzzy logic principles to analyse the at least two candidate amino acid series to determine whether a good result (i.e. a good candidate amino acid series) has been generated, and if not then the previously determined MS spectra are passed to step 202 and a different peptide mass may be selected as a precursor ion for the generation of another $MS^2$ spectrum. A further precursor ion can then be selected from this decision step for ionisation to give an $MS^3$ spectrum (103).

The fuzzy logic principles used in selecting precursor ions comprises the steps of:
  (i) fuzzification of input variables on at least one membership function to give linguistic variables. Typically, between 3 and 7 different terms (e.g. "very low", "low", "low-medium", "medium", "medium-high", "high" and "very high") are used for a linguistic variable;
  (ii) inference of a plurality of rules of a rulebase, each rule having at least one output variable, to define a fuzzy subset for each output variable for each rule; and
  (iii) composition of the fuzzy subsets of inference step (ii) to define a fuzzy output set comprising a single output subset for each of the at least one output variable.

The fuzzy logic process can in certain embodiments finish with step (iii), although in the present embodiment a further step is used to convert the "fuzzy" output to a more finite/discrete and comprehensible value upon which judgements and decisions can be conveniently made. Thus the fuzzy logic principles also comprise the step of:
  (iv) defuzzification of the fuzzy output set to a crisp number.

Figure 2:
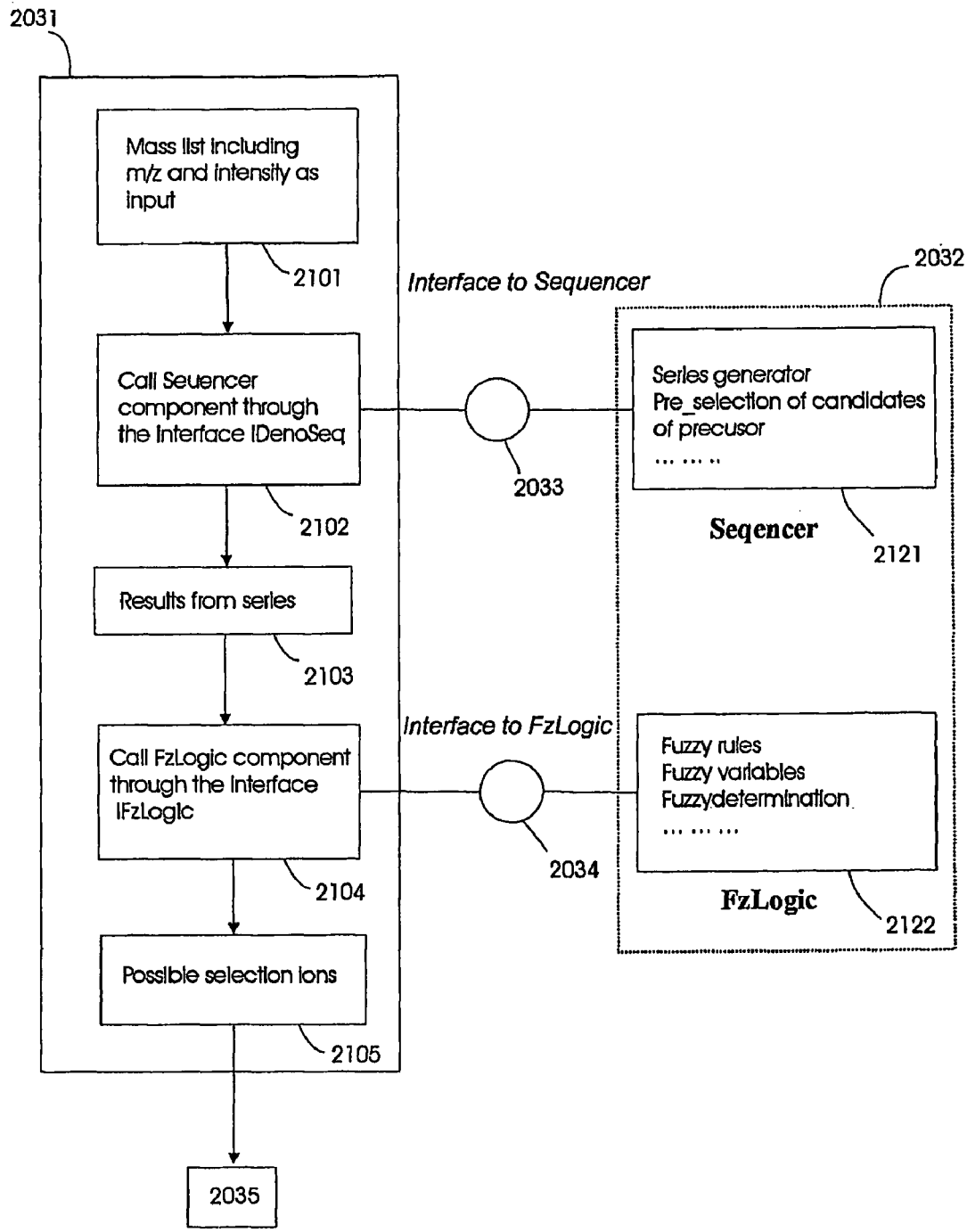
FIG. 2 is a flow chart showing the process of precursor ion selection for a tandem mass spectrum, based upon candidate m/z peak sets derived from a spectrum and fuzzy logic principles.
Figure 3:
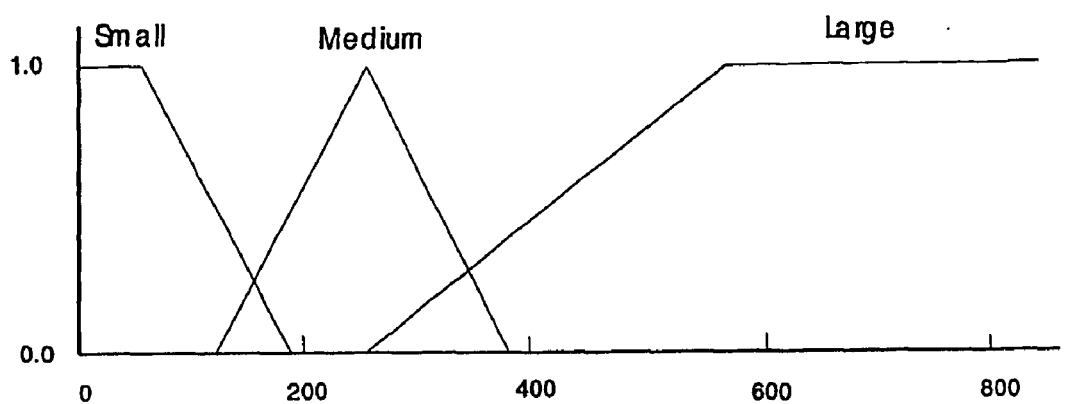
FIG. 3 is a plot of the membership functions for GAP is SMALL, GAP is MEDIUM, and GAP is LARGE.
Figure 4:
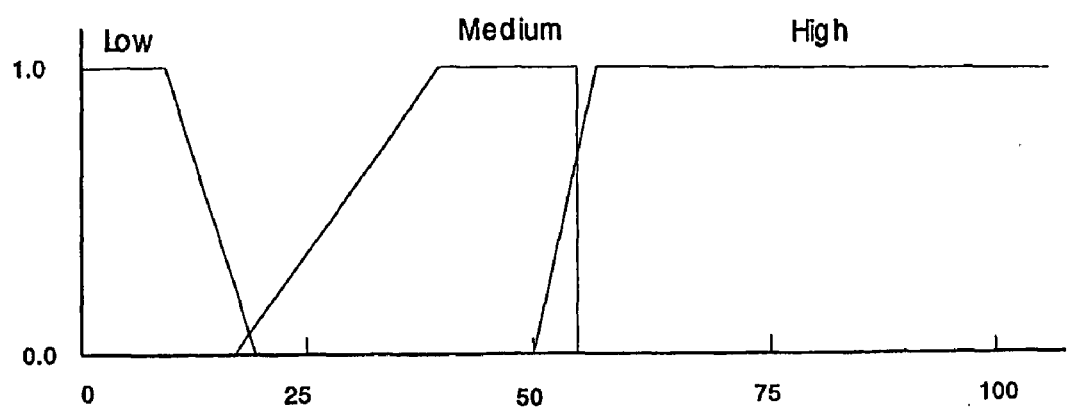
FIG. 4 is a plot of the membership functions for INTENSITY is LOW, INTENSITY is MEDIUM and INTENSITY is HIGH.
Figure 5:
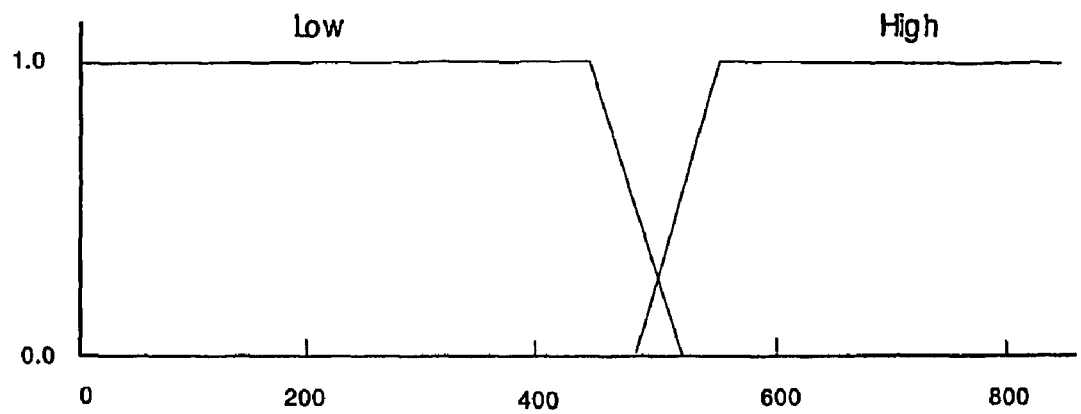
FIG. 5 is a plot of the membership functions for LOW_VALUE_CRITERION is LOW and LOW_VALUE_CRITERION is HIGH.
Figure 6:
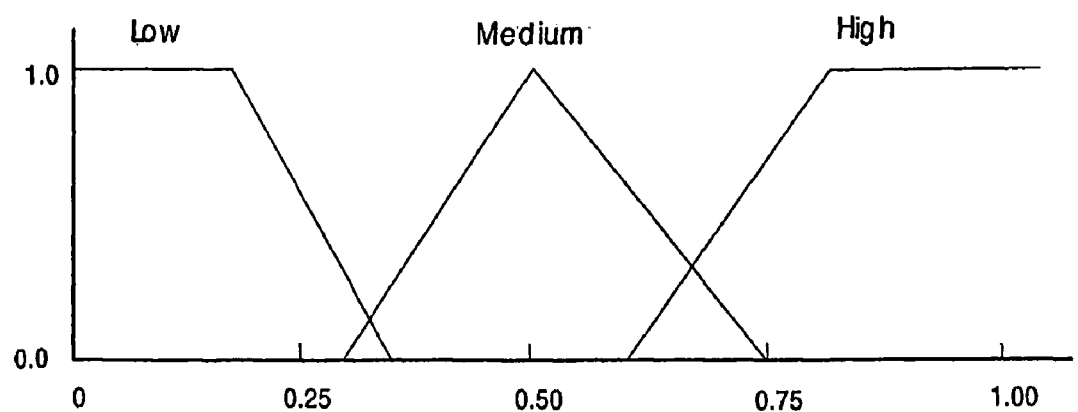
FIG. 6 is a plot of the membership functions for MASS_SERIES is LOW, MASS_SERIES is MEDIUM, and MASS_SERIES is HIGH.

As shown in FIG. 2 program code to perform the above method steps is embedded in a PC DCOM (Distributed Component Object Model) component 2122. This COM component 2122 provides the functions necessary for precursor ion selection. All the functions are wrapped in the component 2122, and a client program 2031 is therefore not provided with the details of how the fuzzy logic algorithms work, but instead accesses the functions provided by the COM component 2122 through a defined interface 2034.

Notably, unlike a $C^{++}$ object, which always runs in the same process space, COM objects can also run across processes or across computers and COM methods can be called across a network. This provides an easy way to link with other systems as desired. Similarly, the Sequencer (WO 03/102572) is also located in a COM component 2121. The client 2031 calls these components 2121, 2122 through the given interfaces 2033, 2034. The client program 2031 drives everything starting from a mass list obtained from $MS^2$ spectra 2101.

The COM server only receives parameters provided from the client 2031 and responds to the requests from the client program 2031. The general steps of a client side interaction with a COM server 2121, 2122 includes function 2102 ('Call Sequencer component through the interface IDenoSeq') and function 2104 ('Call FzLogic component through the interface IFzLogic) of client 2031: (a) starting the server; (b) requesting COM objects 2121, 2122 and interfaces 2033, 2034; (c) originating all method calls to the server; (d) releasing server interfaces, allowing the server to shut down.

Prior to the making of calls to the COM components and initiation of the fuzzy logic methods, pre-selection of candidate m/z peaks is performed by the program code. Specifically, to reduce the number of candidate ion values 2103 input into the COM component 2122 via interface 2034, a pre-selection scheme is applied using the Sequencer COM component 2121. In particular, if a candidate m/z peak at the low end of a candidate m/z peak set is selected but it is actually present in more than one candidate m/z peak set then the longest candidate m/z peak set containing this value is found from those candidate m/z peak sets returned by the Sequencer 2121, and its properties are then used in the fuzzy logic steps. In particular, the analysis of candidate m/z peak sets for the given candidate m/z peak is made with the candidate m/z peak sets being independent of one another (i.e. one candidate m/z peak set is not a subset of any of the other candidate m/z peak sets).

With the longest candidate m/z peak set of which the candidate m/z peak is a member having been determined, the number of amino acids in the candidate m/z peak set is used in the calculation of the MASS_SERIES variable.

In addition, as part of the pre-selection process, each candidate m/z peak which has been chosen for passing to the fuzzy logic COM component 2122 is logged and the same candidate m/z peak is then prevented from being considered again, thus avoiding wasting resources.

The fuzzy logic steps used are described below.

The fuzzification step (i) for each candidate m/z peak in a candidate m/z peak set is performed using the following four input variables representing:
  (a) the number of amino acids corresponding to the difference between the candidate m/z peak value and the closest terminal m/z peak value of the at least one other candidate m/z peak set (GAP);
  (b) the intensity of the candidate m/z peak (INTENSITY);
  (c) the mass represented by the candidate m/z peak value (LOW_VALUE_CRITERION); and
  (d) the number of amino acids in the longest of any putative amino acid sequence corresponding to any candidate m/z peak set containing the candidate m/z peak (MASS_SERIES).

Fuzzification of the input variables is done on the basis of the membership functions shown in FIGS. 3-6.

Inference step (ii) is performed on the basis of the rulebase defined in Table 1A (above).

Where MALDI-QIT spectra are used then it can be important to use a low mass ion as a precursor ion for further fragmentation since it is usually difficult to detect any peaks below one third of the precursor ion mass. Thus the selection of a high mass precursor ion will not give low mass m/z peaks, although the peaks are often necessary in determining a more complete candidate m/z peak set from a b/y series.

Therefore where MALDI-QIT spectra are used, a priority may be given to selection from the lower end of a derived series. In other embodiments, the same factor is taken into account by introducing another variable into the fuzzification step representative of the difference in mass between the candidate m/z peak and the sample polypeptide mass. In this case, a large difference is desirable since it is indicative of a relatively low mass candidate m/z peak, which upon fragmentation should generate additional data for low mass ions. In contrast, the selection of a candidate m/z peak having a small difference in mass compared to the sample polypeptide will probably not generate much if any additional data for low mass ions due to the one-third cut off.

Composition step (iii) is performed using a product composition operator as described above.

Finally, defuzzification step (iv) is performed to give a crisp numerical value for the candidate m/z peak representing its quality or value as a precursor ion for further fragmentation. Specifically, a Centre of Maximum (CoM) method is used. Equation 2 (above) is used in this method, with $Y_{low}=0.175$, $Y_{medium}=0.500$, and $Y_{high}=0.850$. $P_i$ is the weight from the inference results.

At this stage, the candidate m/z peaks will have been assigned a value of "high" or "medium" with weight values greater than 0.5 (the weight value coming from the membership function after defuzzification). The final selection of a candidate m/z peak for further fragmentation is made and that information 2105 is then passed to the mass spectrometry device 2035 and further fragmentation performed of the selected precursor ion at step 103 to generate an $MS^3$ spectrum.

Test on Spectral Data

Testing of the above system is performed using spectral data as detailed below.

A first test is performed using theoretical peptide ion data. The sample data contains all theoretical b, y and a ion series for a given peptide. An example including full b and y series for a peptide is as follows:

b_series ([203.09, 260.11, 423.17, 579.27, 678.34, 791.42, 848.45, 961.53, 1076.56, 1133.58, 1190.6, 1319.64, 1376.66, 1504.76])

y_series ([147.11, 204.13, 333.18, 390.2, 447.22, 562.25, 675.33, 732.35, 845.44, 944.51, 1100.61, 1263.67, 1320.69, 1451.73, 1522.77])]

The sequence of the peptide is: AMGYRVLGID GGEGK (SEQ ID NO: 1) [peptide mass (Mr+H)$^+$: 1522.77 Da].

The underlined ion values in both series are removed from the test file. It is expected that the program can select ion values at 1319.64 for the b series and 1100.61 for the y series. The program derived a result as expected. Both ions are set as 100% high possibility for the selection. Because the data are all theoretical, small tolerance values for MS/MS (0.02) and Peptide (0.1) were used, the tolerance values used here being absolute error values for the expected amino acid mass and precursor mass values allowed in derivation of the series.

TABLE 2

Result from the Program

| | |
|---|---|
| Selected Mass: | 1319.64 |
| Final Output Value: | 0.850 |
| Possible Selection: | High -- 1.000 |
| Selected Mass: | 1100.61 |
| Final Output Value: | 0.850 |
| Possible Selection: | High -- 1.000 |

The results of the test of the sample data is given in Table 2. All the expected ion values can be found in those testing files for these theoretical series and some with larger gaps in the series.

A further test is done on a MALDI-QIT data set. As detailed above, precursor ion selection for further fragmentation is more important for this kind of instrument since correct precursor ion selection can provide more mass ion values to give a more complete ion series list and also add lower mass ions cut off in the $MS^2$ spectra to the series.

There are 27 MALDI-QIT $MS^2$ tryptic peptide spectra available for the testing. Some of them have $MS^3$ spectra, this will be helpful to compare with the results derived from the fuzzy logic selection program.

The mass list for this data is extracted from the MALDI-QIT $MS^2$ spectra, which contain m/z values and intensity. Intensities are normalised on the largest value in the list. The data are first input into a MASCOT search (Matrix Science Ltd, GB) to see how many ion peaks are presented in the list. Table 3 gives an example [Peptide mass (Mr+H)+: 1615.87 Dalton] of the MASCOT search from this set of data. Spectral ion peaks ($MS^2$) match to the theoretical ion values [a, b, y, b−17(b*), b−18(b$^0$), y−17(y*) and y−18(y$^0$)] for the peptide AITIFQERDP ANIK (SEQ ID NO: 2). The matched values are in bold. The tolerance in the search used a larger value up to 0.6 to cover more values. The selection from the program fuzzy logic is expected to fall into these values.

For this example, the program found 22 candidate mass values from the list on the tolerance values: MS/MS-0.1, Peptide-0.1 but only selected one mass value at 1074.63 Da. as a high (weighted 1.0) possible selection. From Table 3, we can see that this is $b_9$ ion value (1074.56+0.07). In this sample, the lowest ion value is 803.45($b_7$, −0.02) in the b series. Further fragmentation at 1074.63 would be expected to give additional ion peaks in the lower mass range. An $MS^3$ spectrum was obtained and is illustrated as the spectrum at the back of FIG. 9. It can be seen that three extra b ion peaks, $b_3$−285.97(−0.21), $b_4$−400.94(−0.32) and $b_5$−546.03(0.3) were found in the $MS^3$ spectrum as indicated by arrows in the figure. This confirms that the fuzzy logic automated precursor ion selection gives a correct selection for a $MS^3$ spectrum. For all 27 samples, at least one correct ion mass is selected from this program, usually a few ions can be derived.

For the LC-QIT data, the selection can apply on the multiple charged ions. For example, a sample got a $MS^2$ spectrum from a triply charged peptide ion (YLEFISDAII HVLHSK— SEQ ID NO: 3, Mr: 1884.01 Daltons) at 629.00. The further selection of precursor for a $MS^3$ gives as 804.93, which is a doubly charged ion, $y_{14}^{++}$. The time for completing this selection is less than 0.2 seconds and the experiment confirmed that a sensible $MS^3$ spectrum is obtained from this selected ion.

Figure 9:
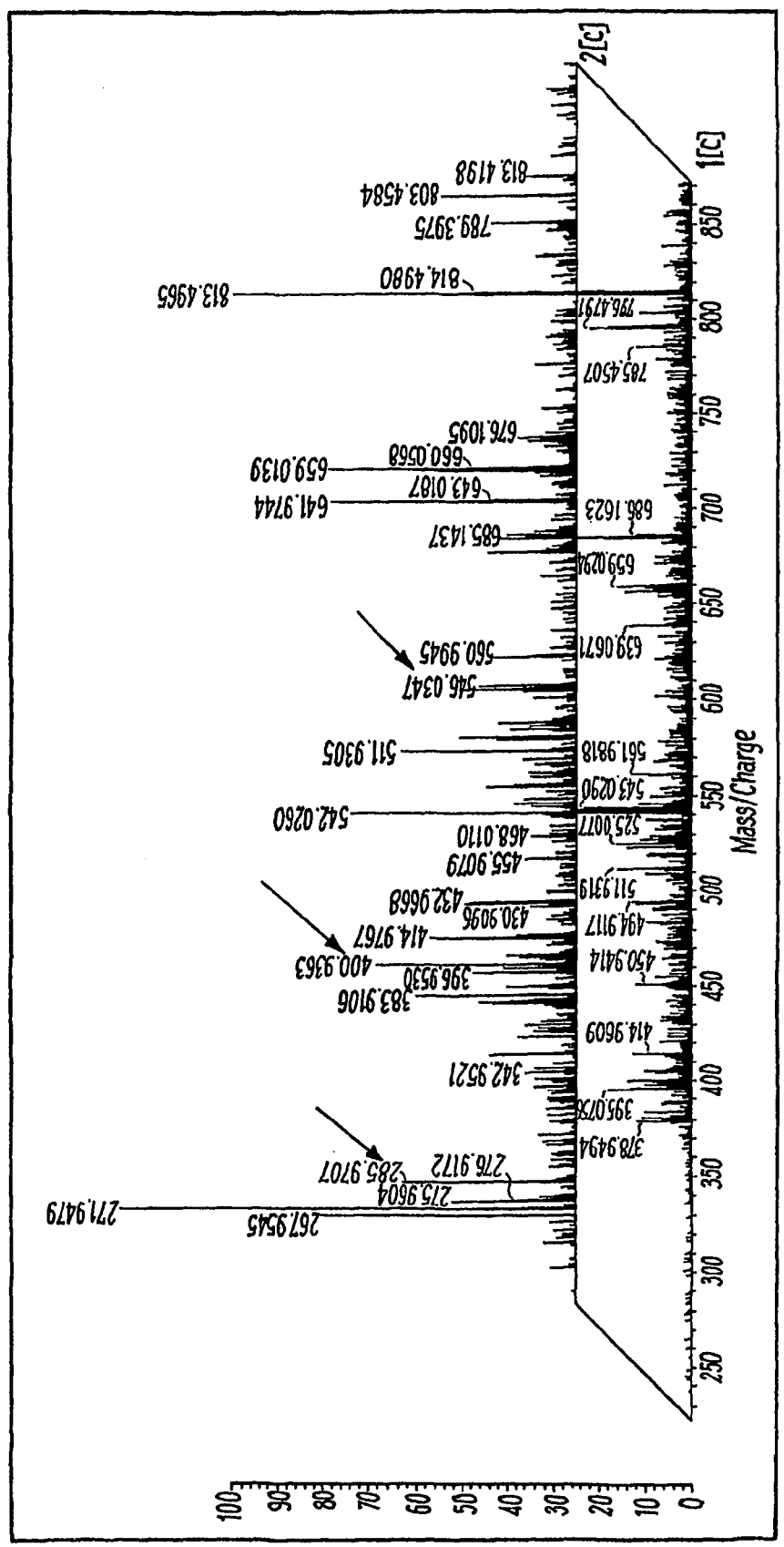
FIG. 9 shows (front) an $MS^2$ spectrum of a test peptide with a mass of 1615 Da and (back) an $MS^3$ spectrum for a 1074 Da fragment from the $MS^2$ spectrum. The arrows indicate ion peaks which are observed in the $MS^3$ spectrum but not in the $MS^2$ spectrum.

Determination of Precursor Ion from $MS^2$ Spectrum of Sample Polypeptide:

Using the method detailed above, precursor ion selection from an $MS^2$ spectrum is performed. Table 4 (below) is a mass list from an $MS^2$ spectrum of a 1615.90 Da precursor ion (as shown in FIG. 9), the table giving masses and intensities.

From the data in Table 4, the system of WO 03/102572 is used to determine de novo putative ion series corresponding to amino acid series, and these are given in Table 5.

The results shown in Table 5 are then filtered as detailed above to give a set of $MS^n$ ions from which the precursor ion is to be selected. This filtered set is shown in Table 6. The columns represent (left to right) ion mass, intensity, gap and mass_series.

The filtered set is then input to the fuzzification step of the fuzzy logic system detailed above to select an ion to act as a precursor ion for further fragmentation, and the results of the fuzzy logic analysis for each of the ions is shows in Table 7. As detailed above, the system comprises the steps of Fuzzification, Inference, Composition and Defuzzification. In the fuzzification step, the input values of GAP, INTENSITY, LOW_VALUE_CRITERION and MASS_SERIES are fuzzified on membership functions (GAP is SMALL etc.). In the inference step, a truth value is calculated for the premise of each rule of a rulebase (Table 1) to give a degree of validity for each rule. In the composition step, the output for each rule of the rulebase is used to create a fuzzy output set (a final output value). In the defuzzification step membership functions for POSSIBLE_SELECTION are applied to the final output value to determine an overall rating for the candidate ion.

The "Selected Mass" is the candidate ion mass being considered. The "Max. Dos" values represent the validity of each of the three terms (POSSIBLE_SELECTION is HIGH, POSSIBLE_SELECTION is MEDIUM, and POSSIBLE_SELECTION is LOW) calculated after inference step (ii) and composition step (iii). The "Final Output Value" is calculated at defuzzification step (iv) using Equations 1 and 2 as detailed above. The "Possible Selection" shows the greatest degree of truth for each of the rule premises POSSIBLE_SELECTION is LOW, POSSIBLE_SELECTION is MEDIUM, and POSSIBLE_SELECTION is HIGH calculated from the final output value (FIG. 7).

Results

As can be seen from the results shown in Table 7 for an example, the result for all of the candidate ions apart from 1074.63 is Low with a degree of truth of 1.000 for each of them. For the candidate ion 1074.63, its POSSIBLE_SELECTION value is HIGH with a degree of truth of 1.000.

Figure 7:
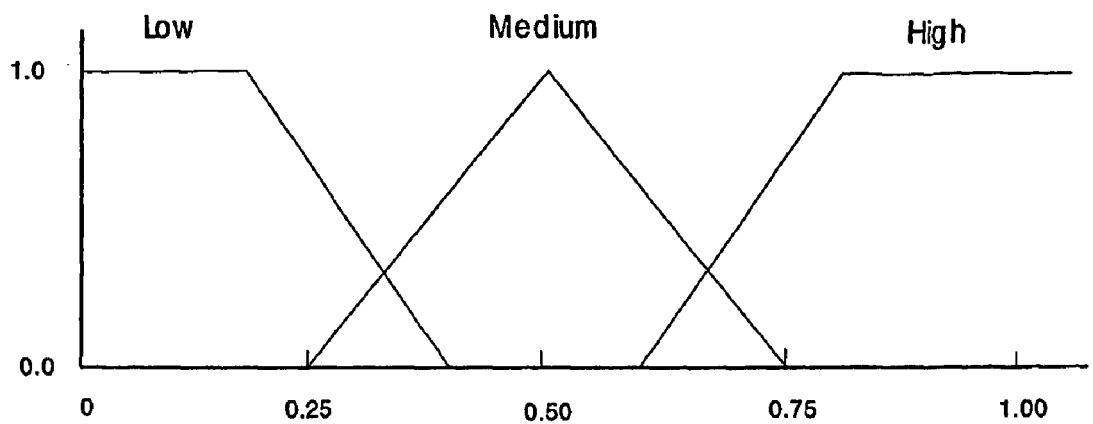
FIG. 7 is a plot of the membership functions for POSSIBLE_SELECTION is LOW, POSSIBLE_SELECTION is MEDIUM, and POSSIBLE_SELECTION is HIGH.
Figure 8:
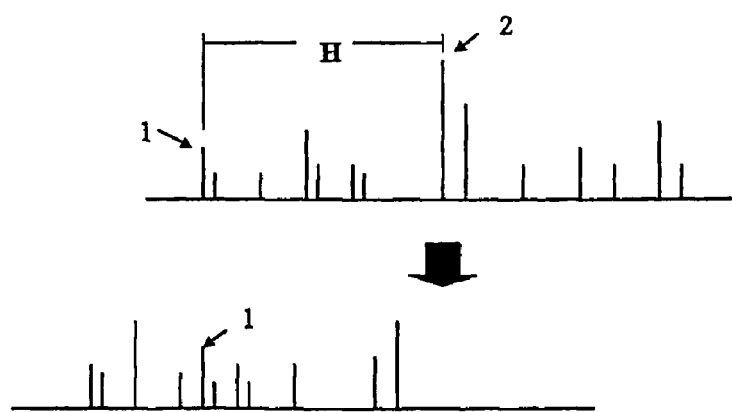
FIG. 8 shows an example of ion peak selection from the end value of a series or strong peak in a series.

As can be seen from FIG. 7, selection of the 1074.63 Da fragment for further fragmentation results in the generation of numerous ion peaks which are detected in the $MS^3$ spectrum but not in the $MS^2$ spectrum. Therefore, the system□s selection of the 1074.63 Da candidate ion from the larger set was a very good one, elucidating additional useful information about the sample polypeptide without requiring user or expert input/assistance.

This example shows that a single ion is selected. Sometimes, more than one ion peak can be selected, each of the selected ion peaks being possible ions for further fragmentation.

TABLE 4

| Ion Mass | Intensity |
|---|---|
| 1615.90 | 100 |
| BEGIN IONS | |
| 378.95 | 1.06 |
| 381.00 | 1.26 |
| 383.92 | 0.99 |
| 387.93 | 0.96 |
| 395.97 | 1.86 |
| 400.92 | 1.36 |
| 404.94 | 1.07 |
| 414.96 | 1.65 |
| 420.97 | 0.70 |
| 432.95 | 0.86 |
| 450.94 | 1.36 |
| 454.98 | 0.72 |
| 473.99 | 0.95 |
| 483.98 | 1.21 |
| 490.97 | 0.84 |
| 491.98 | 1.34 |
| 494.91 | 1.60 |
| 509.97 | 1.17 |
| 511.93 | 1.73 |
| 518.97 | 1.07 |
| 524.01 | 1.90 |
| 528.02 | 1.29 |
| 532.97 | 0.81 |
| 542.03 | 7.46 |
| 549.96 | 0.98 |
| 560.98 | 0.84 |
| 567.99 | 0.85 |
| 579.02 | 0.85 |
| 601.96 | 0.99 |
| 612.03 | 0.63 |
| 622.04 | 0.81 |
| 633.02 | 0.82 |
| 639.07 | 1.48 |
| 641.99 | 0.92 |
| 648.06 | 0.86 |
| 655.06 | 0.76 |
| 657.10 | 1.60 |
| 659.03 | 2.42 |
| 672.11 | 1.11 |
| 675.13 | 0.96 |
| 685.14 | 6.12 |
| 785.45 | 1.17 |
| 789.42 | 0.55 |
| 795.48 | 2.22 |
| 803.45 | 1.23 |
| 813.50 | 11.31 |
| 838.45 | 0.86 |
| 856.43 | 0.80 |
| 873.48 | 1.28 |

TABLE 3

| # | a | b | b* | b⁰ | Seq. | y | y* | y⁰ | # |
|---|---|---|---|---|---|---|---|---|---|
| 1 | 44.05 | 72.04 | | | A | | | | 14 |
| 2 | 157.13 | 185.13 | | | I | 1544.84 | 1527.82 | 1526.83 | 13 |
| 3 | 258.18 | 286.18 | | 268.17 | T | 1431.76 | 1414.73 | 1413.75 | 12 |
| 4 | 371.27 | 399.26 | | 381.25 | I | 1330.71 | 1313.69 | 1312.70 | 11 |
| 5 | 518.33 | 546.33 | | 528.32 | F | 1217.63 | 1200.60 | 1199.62 | 10 |
| 6 | 646.39 | 674.39 | 657.36 | 656.38 | Q | 1070.56 | 1053.53 | 1052.55 | 9 |
| 7 | 775.44 | 803.43 | 786.40 | 785.42 | E | 942.50 | 925.47 | 924.49 | 8 |
| 8 | 931.54 | 959.53 | 942.50 | 941.52 | R | 813.46 | 796.43 | 795.45 | 7 |
| 9 | 1046.56 | 1074.56 | 1057.53 | 1056.55 | D | 657.36 | 640.33 | 639.35 | 6 |
| 10 | 1143.62 | 1171.61 | 1154.58 | 1153.60 | P | 542.33 | 525.30 | | 5 |
| 11 | 1214.65 | 1242.65 | 1225.62 | 1224.64 | A | 445.28 | 428.25 | | 4 |
| 12 | 1328.70 | 1356.69 | 1339.66 | 1338.68 | N | 374.24 | 357.21 | | 3 |
| 13 | 1441.78 | 1469.78 | 1452.75 | 1451.76 | I | 260.20 | 243.17 | | 2 |
| 14 | | | | | K | 147.11 | 130.09 | | 1 | b* indicate b-17 Displacement Series members
b⁰ indicate b-18 Displacement Series members
y* indicate y-17 Displacement Series members
y⁰ indicate y-18 Displacement Series members
Text in bold indicates matched values.

TABLE 4-continued

| Ion Mass | Intensity |
|---|---|
| 891.50 | 0.67 |
| 898.49 | 0.72 |
| 908.51 | 0.74 |
| 916.57 | 0.95 |
| 924.51 | 1.12 |
| 931.58 | 1.17 |
| 936.50 | 0.74 |
| 942.55 | 3.10 |
| 959.59 | 8.53 |
| 977.60 | 7.27 |
| 986.53 | 0.74 |
| 996.58 | 0.74 |
| 1002.63 | 7.39 |
| 1010.63 | 1.03 |
| 1030.60 | 1.78 |
| 1056.60 | 1.26 |
| 1074.63 | 100.00 |
| 1151.65 | 0.62 |
| 1182.62 | 0.88 |
| 1209.61 | 0.62 |
| 1215.72 | 0.91 |
| 1217.69 | 0.89 |
| 1243.70 | 0.70 |
| 1259.76 | 1.04 |
| 1339.78 | 1.34 |
| 1357.76 | 6.06 |
| 1374.81 | 0.97 |
| 1382.81 | 2.80 |
| 1441.88 | 1.40 |
| 1447.72 | 0.93 |
| 1469.87 | 1.63 |
| 1486.84 | 1.15 |
| 1487.88 | 30.56 |
| 1555.92 | 0.95 |
| 1571.93 | 1.73 |
| 1580.91 | 1.88 |
| 1597.98 | 32.53 |
| END IONS | |

TABLE 5

[1580.91]
[1571.93]
[1447.72]
[1441.88, 1597.98]
[1441.88, 1555.92]
[1382.81, 1469.87, 1597.98]
[1339.78, 1486.84]
[1259.76, 1374.81, 1487.88]
[1243.7, 1374.81, 1487.88]
[1243.7, 1357.76, 1486.84]
[1215.72]
[1209.61]
[1151.65]
[996.58, 1182.62]
[977.6, 1074.63]
[891.5]
[873.48, 1010.63]
[873.48, 1002.63]
[873.48, 986.53]
[795.48, 942.55, 1056.6, 1217.69]
[795.48, 924.51]
[795.48, 908.51]
[795.48, 898.49]
[672.11, 803.45, 959.59, 1074.63]
[672.11, 803.45, 959.59, 1056.6, 1217.69]
[672.11, 803.45, 959.59, 1030.6]
[672.11, 803.45, 931.58, 1030.6]
[672.11, 803.45, 931.58, 1002.63]
[672.11, 803.45, 916.57, 1030.6]
[672.11, 785.45, 916.57, 1030.6]
[672.11, 785.45, 898.49]
[672.11, 785.45, 856.43, 959.59, 1074.63]
[672.11, 785.45, 856.43, 959.59, 1056.6, 1217.69]
[672.11, 785.45, 856.43, 959.59, 1030.6]

TABLE 5-continued

[473.99, 601.96, 659.03]
[473.99, 560.98, 675.13, 838.45]
[473.99, 560.98, 675.13, 803.45, 959.59, 1074.63]
[473.99, 560.98, 675.13, 803.45, 959.59, 1056.6, 1217.69]
[473.99, 560.98, 675.13, 803.45, 959.59, 1030.6]
[473.99, 560.98, 675.13, 803.45, 931.58, 1030.6]
[473.99, 560.98, 675.13, 803.45, 931.58, 1002.63]
[473.99, 560.98, 675.13, 803.45, 916.57, 1030.6]
[473.99, 560.98, 675.13, 789.42, 936.5]
[473.99, 560.98, 648.06]
[450.94, 612.03]
[450.94, 579.02]
[450.94, 549.96]
[432.95, 560.98, 675.13, 838.45]
[432.95, 560.98, 675.13, 803.45, 959.59, 1074.63]
[432.95, 560.98, 675.13, 803.45, 959.59, 1056.6, 1217.69]
[432.95, 560.98, 675.13, 803.45, 959.59, 1030.6]
[432.95, 560.98, 675.13, 803.45, 931.58, 1030.6]
[432.95, 560.98, 675.13, 803.45, 931.58, 1002.63]
[432.95, 560.98, 675.13, 803.45, 916.57, 1030.6]
[432.95, 560.98, 675.13, 789.42, 936.5]
[432.95, 560.98, 648.06]
[420.97, 567.99, 655.06]
[420.97, 567.99, 639.07]
[420.97, 549.96]
[420.97, 524.01, 685.14, 813.5, 942.55, 1056.6, 1217.69]
[420.97, 524.01, 685.14, 813.5, 916.57, 1030.6]
[420.97, 524.01, 655.06]
[420.97, 524.01, 639.07]
[420.97, 491.98, 655.06]
[420.97, 491.98, 648.06]
[420.97, 491.98, 639.07]
[420.97, 491.98, 579.02]
[414.96, 528.02, 675.13, 838.45]
[414.96, 528.02, 675.13, 803.45, 959.59, 1074.63]
[414.96, 528.02, 675.13, 803.45, 959.59, 1056.6, 1217.69]
[414.96, 528.02, 675.13, 803.45, 959.59, 1030.6]
[414.96, 528.02, 675.13, 803.45, 931.58, 1030.6]
[414.96, 528.02, 675.13, 803.45, 931.58, 1002.63]
[414.96, 528.02, 675.13, 803.45, 916.57, 1030.6]
[414.96, 528.02, 675.13, 789.42, 936.5]
[414.96, 528.02, 659.03]
[414.96, 528.02, 657.1, 813.5, 942.55, 1056.6, 1217.69]
[414.96, 528.02, 657.1, 813.5, 916.57, 1030.6]
[414.96, 528.02, 657.1, 785.45, 916.57, 1030.6]
[414.96, 528.02, 657.1, 785.45, 898.49]
[414.96, 528.02, 657.1, 785.45, 856.43, 959.59, 1074.63]
[414.96, 528.02, 657.1, 785.45, 856.43, 959.59, 1056.6, 1217.69]
[414.96, 528.02, 657.1, 785.45, 856.43, 959.59, 1030.6]
[414.96, 528.02, 641.99]
[414.96, 511.93, 675.13, 838.45]
[414.96, 511.93, 675.13, 803.45, 959.59, 1074.63]
[414.96, 511.93, 675.13, 803.45, 959.59, 1056.6, 1217.69]
[414.96, 511.93, 675.13, 803.45, 959.59, 1030.6]
[414.96, 511.93, 675.13, 803.45, 931.58, 1030.6]
[414.96, 511.93, 675.13, 803.45, 931.58, 1002.63]
[414.96, 511.93, 675.13, 803.45, 916.57, 1030.6]
[414.96, 511.93, 675.13, 789.42, 936.5]
[414.96, 511.93, 659.03]
[404.94, 567.99, 655.06]
[404.94, 567.99, 639.07]
[404.94, 560.98, 675.13, 838.45]
[404.94, 560.98, 675.13, 803.45, 959.59, 1074.63]
[404.94, 560.98, 675.13, 803.45, 959.59, 1056.6, 1217.69]
[404.94, 560.98, 675.13, 803.45, 959.59, 1030.6]
[404.94, 560.98, 675.13, 803.45, 931.58, 1030.6]
[404.94, 560.98, 675.13, 803.45, 931.58, 1002.63]
[404.94, 560.98, 675.13, 803.45, 916.57, 1030.6]
[404.94, 560.98, 675.13, 789.42, 936.5]
[404.94, 560.98, 648.06]
[404.94, 542.03, 657.1, 813.5, 942.55, 1056.6, 1217.69]
[404.94, 542.03, 657.1, 813.5, 916.57, 1030.6]
[404.94, 542.03, 657.1, 785.45, 916.57, 1030.6]
[404.94, 542.03, 657.1, 785.45, 898.49]
[404.94, 542.03, 657.1, 785.45, 856.43, 959.59, 1074.63]
[404.94, 542.03, 657.1, 785.45, 856.43, 959.59, 1056.6, 1217.69]
[404.94, 542.03, 657.1, 785.45, 856.43, 959.59, 1030.6]
[404.94, 542.03, 655.06]
[404.94, 542.03, 639.07]
[404.94, 532.97, 648.06]

TABLE 5-continued

[404.94, 518.97, 675.13, 838.45]
[404.94, 518.97, 675.13, 803.45, 959.59, 1074.63]
[404.94, 518.97, 675.13, 803.45, 959.59, 1056.6, 1217.69]
[404.94, 518.97, 675.13, 803.45, 959.59, 1030.6]
[404.94, 518.97, 675.13, 803.45, 931.58, 1030.6]
[404.94, 518.97, 675.13, 803.45, 931.58, 1002.63]
[404.94, 518.97, 675.13, 803.45, 916.57, 1030.6]
[404.94, 518.97, 675.13, 789.42, 936.5]
[404.94, 518.97, 648.06]
[404.94, 518.97, 633.02, 789.42, 936.5]
[404.94, 518.97, 622.04]
[404.94, 491.98, 655.06]
[404.94, 491.98, 648.06]
[404.94, 491.98, 639.07]
[404.94, 491.98, 579.02]
[400.92]
[395.97, 532.97, 648.06]
[395.97, 524.01, 685.14, 813.5, 942.55, 1056.6, 1217.69]
[395.97, 524.01, 685.14, 813.5, 916.57, 1030.6]
[395.97, 524.01, 655.06]
[395.97, 524.01, 639.07]
[395.97, 509.97, 657.1, 813.5, 942.55, 1056.6, 1217.69]
[395.97, 509.97, 657.1, 813.5, 916.57, 1030.6]
[395.97, 509.97, 657.1, 785.45, 916.57, 1030.6]
[395.97, 509.97, 657.1, 785.45, 898.49]
[395.97, 509.97, 657.1, 785.45, 856.43, 959.59, 1074.63]
[395.97, 509.97, 657.1, 785.45, 856.43, 959.59, 1056.6, 1217.69]
[395.97, 509.97, 657.1, 785.45, 856.43, 959.59, 1030.6]
[395.97, 509.97, 639.07]
[395.97, 494.91, 641.99]
[387.93, 518.97, 675.13, 838.45]
[387.93, 518.97, 675.13, 803.45, 959.59, 1074.63]
[387.93, 518.97, 675.13, 803.45, 959.59, 1056.6, 1217.69]
[387.93, 518.97, 675.13, 803.45, 959.59, 1030.6]
[387.93, 518.97, 675.13, 803.45, 931.58, 1030.6]
[387.93, 518.97, 675.13, 803.45, 931.58, 1002.63]
[387.93, 518.97, 675.13, 803.45, 916.57, 1030.6]
[387.93, 518.97, 675.13, 789.42, 936.5]
[387.93, 518.97, 648.06]
[387.93, 518.97, 633.02, 789.42, 936.5]
[387.93, 518.97, 622.04]
[387.93, 490.97, 622.04]
[383.92, 511.93, 675.13, 838.45]
[383.92, 511.93, 675.13, 803.45, 959.59, 1074.63]
[383.92, 511.93, 675.13, 803.45, 959.59, 1056.6, 1217.69]
[383.92, 511.93, 675.13, 803.45, 959.59, 1030.6]
[383.92, 511.93, 675.13, 803.45, 931.58, 1030.6]
[383.92, 511.93, 675.13, 803.45, 931.58, 1002.63]
[383.92, 511.93, 675.13, 803.45, 916.57, 1030.6]
[383.92, 511.93, 675.13, 789.42, 936.5]
[383.92, 511.93, 659.03]
[383.92, 454.98, 601.96, 659.03]
[383.92, 454.98, 567.99, 655.06]
[383.92, 454.98, 567.99, 639.07]
[383.92, 454.98, 542.03, 657.1, 813.5, 942.55, 1056.6, 1217.69]
[383.92, 454.98, 542.03, 657.1, 813.5, 916.57, 1030.6]
[383.92, 454.98, 542.03, 657.1, 785.45, 916.57, 1030.6]
[383.92, 454.98, 542.03, 657.1, 785.45, 898.49]
[383.92, 454.98, 542.03, 657.1, 785.45, 856.43, 959.59, 1074.63]
[383.92, 454.98, 542.03, 657.1, 785.45, 856.43, 959.59, 1056.6, 1217.69]
[383.92, 454.98, 542.03, 657.1, 785.45, 856.43, 959.59, 1030.6]
[383.92, 454.98, 542.03, 655.06]
[383.92, 454.98, 542.03, 639.07]
[383.92, 454.98, 511.93, 675.13, 838.45]
[383.92, 454.98, 511.93, 675.13, 803.45, 959.59, 1074.63]
[383.92, 454.98, 511.93, 675.13, 803.45, 959.59, 1056.6, 1217.69]
[383.92, 454.98, 511.93, 675.13, 803.45, 959.59, 1030.6]
[383.92, 454.98, 511.93, 675.13, 803.45, 931.58, 1030.6]
[383.92, 454.98, 511.93, 675.13, 803.45, 931.58, 1002.63]
[383.92, 454.98, 511.93, 675.13, 803.45, 916.57, 1030.6]
[383.92, 454.98, 511.93, 675.13, 789.42, 936.5]
[383.92, 454.98, 511.93, 659.03]
[381, 542.03, 657.1, 813.5, 942.55, 1056.6, 1217.69]
[381, 542.03, 657.1, 813.5, 916.57, 1030.6]
[381, 542.03, 657.1, 785.45, 916.57, 1030.6]
[381, 542.03, 657.1, 785.45, 898.49]
[381, 542.03, 657.1, 785.45, 856.43, 959.59, 1074.63]
[381, 542.03, 657.1, 785.45, 856.43, 959.59, 1056.6, 1217.69]
[381, 542.03, 657.1, 785.45, 856.43, 959.59, 1030.6]
[381, 542.03, 655.06]
[381, 542.03, 639.07]
[381, 528.02, 675.13, 838.45]
[381, 528.02, 675.13, 803.45, 959.59, 1074.63]
[381, 528.02, 675.13, 803.45, 959.59, 1056.6, 1217.69]
[381, 528.02, 675.13, 803.45, 959.59, 1030.6]
[381, 528.02, 675.13, 803.45, 931.58, 1030.6]
[381, 528.02, 675.13, 803.45, 931.58, 1002.63]
[381, 528.02, 675.13, 803.45, 916.57, 1030.6]
[381, 528.02, 675.13, 789.42, 936.5]
[381, 528.02, 659.03]
[381, 528.02, 657.1, 813.5, 942.55, 1056.6, 1217.69]
[381, 528.02, 657.1, 813.5, 916.57, 1030.6]
[381, 528.02, 657.1, 785.45, 916.57, 1030.6]
[381, 528.02, 657.1, 785.45, 898.49]
[381, 528.02, 657.1, 785.45, 856.43, 959.59, 1074.63]
[381, 528.02, 657.1, 785.45, 856.43, 959.59, 1056.6, 1217.69]
[381, 528.02, 657.1, 785.45, 856.43, 959.59, 1030.6]
[381, 528.02, 641.99]
[381, 511.93, 675.13, 838.45]
[381, 511.93, 675.13, 803.45, 959.59, 1074.63]
[381, 511.93, 675.13, 803.45, 959.59, 1056.6, 1217.69]
[381, 511.93, 675.13, 803.45, 959.59, 1030.6]
[381, 511.93, 675.13, 803.45, 931.58, 1030.6]
[381, 511.93, 675.13, 803.45, 931.58, 1002.63]
[381, 511.93, 675.13, 803.45, 916.57, 1030.6]
[381, 511.93, 675.13, 789.42, 936.5]
[381, 511.93, 659.03]
[381, 509.97, 657.1, 813.5, 942.55, 1056.6, 1217.69]
[381, 509.97, 657.1, 813.5, 916.57, 1030.6]
[381, 509.97, 657.1, 785.45, 916.57, 1030.6]
[381, 509.97, 657.1, 785.45, 898.49]
[381, 509.97, 657.1, 785.45, 856.43, 959.59, 1074.63]
[381, 509.97, 657.1, 785.45, 856.43, 959.59, 1056.6, 1217.69]
[381, 509.97, 657.1, 785.45, 856.43, 959.59, 1030.6]
[381, 509.97, 639.07]
[381, 494.91, 641.99]
[381, 483.98, 612.03]
[378.95, 542.03, 657.1, 813.5, 942.55, 1056.6, 1217.69]
[378.95, 542.03, 657.1, 813.5, 916.57, 1030.6]
[378.95, 542.03, 657.1, 785.45, 916.57, 1030.6]
[378.95, 542.03, 657.1, 785.45, 898.49]
[378.95, 542.03, 657.1, 785.45, 856.43, 959.59, 1074.63]
[378.95, 542.03, 657.1, 785.45, 856.43, 959.59, 1056.6, 1217.69]
[378.95, 542.03, 657.1, 785.45, 856.43, 959.59, 1030.6]
[378.95, 542.03, 655.06]
[378.95, 542.03, 639.07]
[378.95, 509.97, 657.1, 813.5, 942.55, 1056.6, 1217.69]
[378.95, 509.97, 657.1, 813.5, 916.57, 1030.6]
[378.95, 509.97, 657.1, 785.45, 916.57, 1030.6]
[378.95, 509.97, 657.1, 785.45, 898.49]
[378.95, 509.97, 657.1, 785.45, 856.43, 959.59, 1074.63]
[378.95, 509.97, 657.1, 785.45, 856.43, 959.59, 1056.6, 1217.69]
[378.95, 509.97, 657.1, 785.45, 856.43, 959.59, 1030.6]
[378.95, 509.97, 639.07]
[378.95, 491.98, 655.06]
[378.95, 491.98, 648.06]
[378.95, 491.98, 639.07]
[378.95, 491.98, 579.02]

TABLE 6

| Ion Mass | Intensity | Gap | Mass_Series |
| --- | --- | --- | --- |
| 1339.78 | 1.34 | 124 | 0.17 |
| 1259.76 | 1.04 | 44 | 0.25 |
| 1243.70 | 0.70 | 27 | 0.25 |
| 1215.72 | 0.91 | 6 | 0.08 |
| 1209.61 | 0.62 | 26 | 0.08 |
| 1151.65 | 0.62 | 77 | 0.08 |
| 996.58 | 0.74 | 10 | 0.17 |
| 977.60 | 7.27 | 41 | 0.17 |
| 672.11 | 1.11 | 13 | 0.50 |
| 473.99 | 0.95 | 73 | 0.58 |
| 450.94 | 1.36 | 50 | 0.17 |
| 432.95 | 0.86 | 32 | 0.58 |
| 420.97 | 0.70 | 20 | 0.58 |
| 414.96 | 1.65 | 14 | 0.67 |

TABLE 6-continued

| Ion Mass | Intensity | Gap | Mass_Series |
|---|---|---|---|
| 404.94 | 1.07 | 4 | 0.67 |
| 400.92 | 1.36 | 240 | 0.08 |
| 395.97 | 1.86 | 240 | 0.67 |
| 387.93 | 0.96 | 240 | 0.58 |
| 383.92 | 0.99 | 240 | 0.75 |
| 381.00 | 1.26 | 240 | 0.67 |
| 378.95 | 1.06 | 240 | 0.67 |
| 1074.63 | 100.00 | 400 | 0.17 |

TABLE 7

| | |
|---|---|
| Selected Mass: | 1339.78 |
| Max. Dos: | 0.265 0.000 0.000 |
| Final Output Value: | 0.056 |
| Possible Selection: | Low -- 1.000 |
| Selected Mass: | 1259.76 |
| Max. Dos: | 0.350 0.000 0.000 |
| Final Output Value: | 0.073 |
| Possible Selection: | Low -- 1.000 |
| Selected Mass: | 1243.70 |
| Max. Dos: | 0.350 0.000 0.000 |
| Final Output Value: | 0.073 |
| Possible Selection: | Low -- 1.000 |
| Selected Mass: | 996.58 |
| Max. Dos: | 1.000 0.000 0.000 |
| Final Output Value: | 0.175 |
| Possible Selection: | Low -- 1.000 |
| Selected Mass: | 977.60 |
| Max. Dos: | 1.000 0.000 0.000 |
| Final Output Value: | 0.175 |
| Possible Selection: | Low -- 1.000 |
| Selected Mass: | 873.48 |
| Max. Dos: | 1.000 0.000 0.000 |
| Final Output Value: | 0.175 |
| Possible Selection: | Low -- 1.000 |
| Selected Mass: | 795.48 |
| Max. Dos: | 0.388 0.000 0.000 |
| Final Output Value: | 0.082 |
| Possible Selection: | Low -- 1.000 |
| Selected Mass: | 789.42 |
| Max. Dos: | 0.435 0.000 0.000 |
| Final Output Value: | 0.175 |
| Possible Selection: | Low -- 1.000 |
| Selected Mass: | 785.45 |
| Max. Dos: | 0.466 0.000 0.000 |
| Final Output Value: | 0.175 |
| Possible Selection: | Low -- 1.000 |
| Selected Mass: | 601.96 |
| Max. Dos: | 1.000 0.000 0.000 |
| Final Output Value: | 0.175 |
| Possible Selection: | Low -- 1.000 |

TABLE 7-continued

| | |
|---|---|
| Selected Mass: | 494.91 |
| Max. Dos: | 0.102 0.000 0.000 |
| Final Output Value: | 0.021 |
| Possible Selection: | Low -- 1.000 |
| Selected Mass: | 473.99 |
| Max. Dos: | 0.520 0.000 0.000 |
| Final Output Value: | 0.175 |
| Possible Selection: | Low -- 1.000 |
| Selected Mass: | 450.94 |
| Max. Dos: | 0.975 0.000 0.000 |
| Final Output Value: | 0.175 |
| Possible Selection: | Low -- 1.000 |
| Selected Mass: | 432.95 |
| Max. Dos: | 0.750 0.000 0.000 |
| Final Output Value: | 0.175 |
| Possible Selection: | Low -- 1.000 |
| Selected Mass: | 420.97 |
| Max. Dos: | 0.750 0.000 0.000 |
| Final Output Value: | 0.175 |
| Possible Selection: | Low -- 1.000 |
| Selected Mass: | 414.96 |
| Max. Dos: | 0.750 0.000 0.000 |
| Final Output Value: | 0.175 |
| Possible Selection: | Low -- 1.000 |
| Selected Mass: | 404.94 |
| Max. Dos: | 0.750 0.000 0.000 |
| Final Output Value: | 0.175 |
| Possible Selection: | Low -- 1.000 |
| Selected Mass: | 395.97 |
| Max. Dos: | 0.750 0.000 0.000 |
| Final Output Value: | 0.175 |
| Possible Selection: | Low -- 1.000 |
| Selected Mass: | 387.93 |
| Max. Dos: | 0.750 0.000 0.000 |
| Final Output Value: | 0.175 |
| Possible Selection: | Low -- 1.000 |
| Selected Mass: | 383.92 |
| Max. Dos: | 0.350 0.000 0.000 |
| Final Output Value: | 0.073 |
| Possible Selection: | Low -- 1.000 |
| Selected Mass: | 381.00 |
| Max. Dos: | 0.750 0.000 0.000 |
| Final Output Value: | 0.175 |
| Possible Selection: | Low -- 1.000 |
| Selected Mass: | 378.95 |
| Max. Dos: | 0.750 0.000 0.000 |
| Final Output Value: | 0.175 |
| Possible Selection: | Low -- 1.000 |
| Selected Mass: | 1074.63 |
| Max. Dos: | 0.000 0.000 0.486 |
| Final Output Value: | 0.850 |
| Possible Selection: | High -- 1.000 |

---

The invention claimed is:

1. A system for selecting at least one m/z peak of a soft ionisation mass spectrum of a partially degraded sample polypeptide for fragmentation, comprising:
   (a) a memory for storing machine instructions for analysing using an artificial intelligence technique the m/z peaks of an at least two candidate m/z peak sets to select at least one m/z peak for fragmentation, said at least two candidate m/z peak sets determined from said soft ionisation mass spectrum of said partially degraded sample polypeptide, said soft ionisation mass spectrum comprising a set of m/z peaks of ion species obtained from said partially degraded sample polypeptide, each m/z peak in each candidate m/z peak set differing from its at least one neighbour by the mass of an amino acid, and a putative amino acid sequence being determined from each candidate m/z peak set, each amino acid sequence being that of the amino acids which correspond to the mass differences between each m/z peak and its at least one neighbour; and
   (b) a processor for analysing using the fuzzy logic principles said m/z peaks of said at least two candidate m/z peak sets, to select at least one m/z peak for fragmentation.

2. A system according to claim 1 additionally including:
   a memory for storing a fuzzy logic rulebase for use with said fuzzy logic principles of said machine instructions;
   wherein the processor is coupled to said memory, said processor executing said machine instructions with reference to said fuzzy logic rulebase, causing said processor to determine at least one m/z peak of said soft ionisation mass spectrum of said partially degraded sample polypeptide for fragmentation.

3. A system according to claim 1, additionally comprising:
   (i) data input means for inputting data representing said soft ionisation mass spectrum; and
   (ii) output means for outputting the output of said processor.

4. A system according to claim 1, additionally comprising a mass spectrometer.

5. A system according to claim 2, wherein the rulebase can further comprise gathering knowledge from experimental data through training by data mining methods.

6. A system according to claim 5, wherein the data mining methods include at least one of the following:
   neural networks;
   decision tree; and
   rule deduction algorithms.

* * * * *

SEQUENCE LISTING

<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<221> NAME/KEY: Artificial Sequence
<223> OTHER INFORMATION: Test synthetic sequence

<400> SEQUENCE: 1

Ala Met Gly Tyr Arg Val Leu Gly Ile Asp Gly Gly Glu Gly Lys
1               5                   10                  15

<210> SEQ ID NO 2

-continued

```
<211> LENGTH: 14
<212> TYPE: PRT
<213> ORGANISM: Artificial Sequence
<220> FEATURE:
<221> NAME/KEY: Artificial Sequence
<223> OTHER INFORMATION: Test synthetic sequence

<400> SEQUENCE: 2

Ala Ile Thr Ile Phe Gln Glu Arg Asp Pro Ala Asn Ile Lys
1               5                   10

<210> SEQ ID NO 3
<211> LENGTH: 16
<212> TYPE: PRT
<213> ORGANISM: Artificial Sequence
<220> FEATURE:
<221> NAME/KEY: Artificial Sequence
<223> OTHER INFORMATION: Test synthetic sequence

<400> SEQUENCE: 3

Tyr Leu Glu Phe Ile Ser Asp Ala Ile Ile His Val Leu His Ser Lys
1               5                   10                  15
```